United States Patent
Van Vliet et al.

(10) Patent No.: US 9,273,333 B2
(45) Date of Patent: Mar. 1, 2016

(54) PROCESS FOR THE PREPARATION OF INTERMEDIATES OF HMG-COA REDUCTASE INHIBITORS

(71) Applicant: Mylan Laboratories LTD, Hyderabad (IN)

(72) Inventors: Michiel Christian Alexander Van Vliet, Hyderabad (IN); Willem Robert Klaas Schoevaart, Hyderabad (IN); Madhuresh Kumar Sethi, Hyderabad (IN); Sanjay Mahajan, Hyderabad (IN); Bhairaiah Mara, Hyderabad (IN)

(73) Assignee: Mylan Laboratories LTD, Hyderbad (IN)

( * ) Notice: Subject to any disclaimer, the term of this patent is extended or adjusted under 35 U.S.C. 154(b) by 0 days.

(21) Appl. No.: 14/288,999

(22) Filed: May 28, 2014

(65) Prior Publication Data

US 2014/0349350 A1    Nov. 27, 2014

Related U.S. Application Data

(63) Continuation of application No. PCT/IN2012/000770, filed on Nov. 26, 2012.

(51) Int. Cl.

| | | |
|---|---|---|
| C12P 17/12 | (2006.01) | |
| C12P 7/42 | (2006.01) | |
| C12P 7/44 | (2006.01) | |
| C12P 7/62 | (2006.01) | |
| C12P 13/02 | (2006.01) | |
| C07D 215/14 | (2006.01) | |
| C07D 239/42 | (2006.01) | |
| C07C 231/12 | (2006.01) | |
| C07F 7/18 | (2006.01) | |
| C12P 9/00 | (2006.01) | |

(52) U.S. Cl.
CPC .............. *C12P 17/12* (2013.01); *C07C 231/12* (2013.01); *C07D 215/14* (2013.01); *C07D 239/42* (2013.01); *C07F 7/1844* (2013.01); *C12P 7/42* (2013.01); *C12P 7/44* (2013.01); *C12P 7/62* (2013.01); *C12P 9/00* (2013.01); *C12P 13/02* (2013.01)

(58) Field of Classification Search
None
See application file for complete search history.

(56) References Cited

FOREIGN PATENT DOCUMENTS

WO    2008130638    10/2008

OTHER PUBLICATIONS

Puertas, S. et al., "Enantioselective Enzymatic Aminolysis and Ammonolysis of Dimethyl 3-Hydroxyglutarate. Synthesis of (R)-4-Amino-3-hydroxybutanoic Acid", The Journal of Organic Chemistry, vol. 61, No. 17, 1996, pp. 6024-6027.
Written Opinion of the International Searching Authority, Serial No. PCT/IN2012/000770
Jacobsen, E.E. et al., "Enantioselective enzymatic preparation of chiral glutaric monocarboxylic acids and amides", Journal of Molecular Catalysis. B. Enzymatic, vol. 21, No. 1-2, 2003, pp. 55-58, XP002648570.
Liljeblad, A. et al., "Biocatalysis in the Preparation of the Statin Side Chain", Current Organic Synthesis, vol. 6, No. 4, Nov. 2009, pp. 362-379, XP008165228.

*Primary Examiner* — Nashaat Nashed
(74) *Attorney, Agent, or Firm* — Beck & Thomas, P.C.

(57) ABSTRACT

The present invention relates to an improved process for the preparation of compound of Formula-II, which is an intermediate in the preparation of HMG-CoA reductase inhibitors.

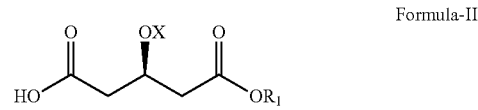

Formula-II wherein X is hydrogen or hydroxy protecting group and $R_1$ is carboxyl protecting group.

9 Claims, No Drawings

PROCESS FOR THE PREPARATION OF INTERMEDIATES OF HMG-COA REDUCTASE INHIBITORS

This is a continuation of International Application PCT/IN2012/000770, with an international filing date of Nov. 28, 2012, which in turn claims priority to Indian Application No. 4102/CHE/2011, filed Nov. 28, 2011 and incorporates by reference in its entirety the PCT and Indian Application into the current nonprovisional application.

FIELD OF THE INVENTION

The present invention relates to novel process for the preparation of pentanoic acid derivatives, used as intermediates of HMG-CoA reductase inhibitors, and further conversion to HMG-CoA reductase inhibitors.

BACKGROUND OF THE INVENTION

The HMG-CoA reductase inhibitors (Statins) have been used in reducing blood levels of LDL cholesterol. Cholesterol is produced via the mevalonic acid pathway. Reducing the formation of mevalonic acid, a precursor to cholesterol, leads to a corresponding decrease in hepatic cholesterol biosynthesis with a reduction in the cellular pool of cholesterol. The HMG-CoA reductase inhibitors (Statins) represented by the following general Formula-I,

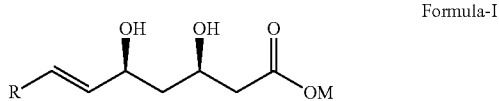

Formula-I wherein R is a residue of HMG-CoA reductase inhibitor; M represents hydrogen or pharmaceutically acceptable salts like sodium, potassium, magnesium and calcium.

Bis[(E)-7-[4-(4-fluorophenyl)-6-isopropyl-2-[methyl (methylsulfonyl)amino]pyrimidin-5-yl](3R,5S)-3,5-dihydroxyhept-6-enoic acid]Calcium Salt of Formula-A (Rosuvastatin Calcium) is an HMG-CoA reductase inhibitor, developed by shionogi for the treatment of hyperlipidemia.

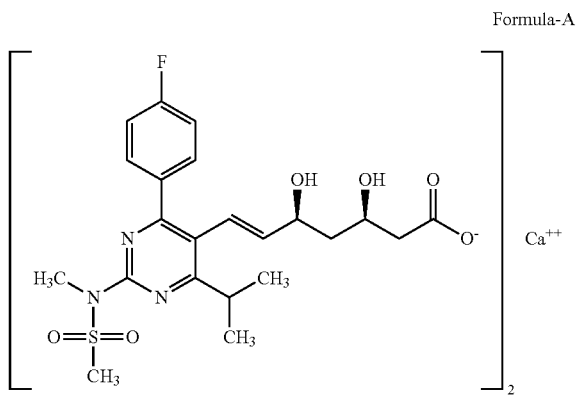

Formula-A

Rosuvastatin calcium is marketed under the proprietary name CRESTOR for treatment of mammals such as human and administrated as daily dosage form of 5 mg, 10 mg, 20 mg and 40 mg.

Rosuvastatin and its pharmaceutically acceptable salts were first disclosed in European patent publication EP 0521471. It also discloses process for the preparation of Rosuvastatin calcium.

Bis{(3R,5S,6E)-7-[2-cyclopropyl-4-(4-fluorophenyl)-3-quinolyl]-3,5-dihydroxy-6-heptenoate} monocalcium of Formula-B (Pitavastatin Calcium) is an HMG-CoA reductase inhibitor, developed by Nissan Chemical Industries for the treatment of hyperlipidemia.

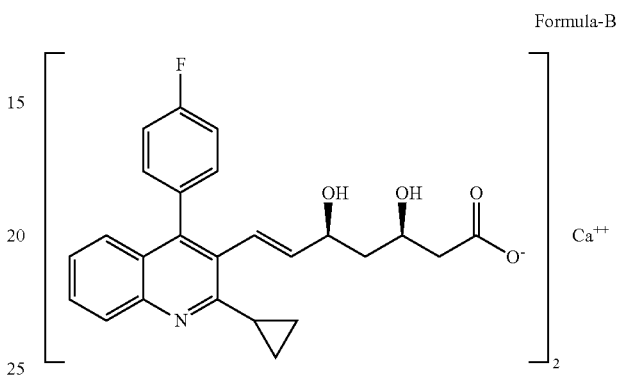

Formula-B

Pitavastatin and its pharmaceutically acceptable salts were first disclosed in European patent publication EP 0304063. It also discloses process for the preparation of Pitavastatin sodium.

U.S. Pat. No. 5,260,440 and PCT publication No. WO 03/097614, disclose the synthesis of Rosuvastatin from the intermediate 3(R)-3(tert-butyldimethylsilyloxy)-5-oxo-6-triphenyl-phosphoranylidene hexanoate.

PCT publication No. WO 03/087112 discloses the synthesis of Rosuvastatin from intermediate, (3R)-3-(t-butyldimethylsilyloxy)-6-dimethoxyphosphinyl-5-oxo-hexanoate.

U.S. Pat. No. 5,117,039 discloses the process for the preparation of (3R)-3-[(tert-butyldimethylsilyl)oxy]pentanedioic acid, 1-[(R)-Mandelic acid]Ester by the ring opening of 3-[(tert-Butyldimethylsilyl)oxy]pentanedioic anhydride using benzyl D-mandelate which gives less yields along with impurities.

US 20090076292 discloses process for the preparation of Rosuvastatin by using the intermediates 3(R)-3(tert-butyldimethylsilyloxy)-5-oxo-6-triphenyl-phosphoranylidene hexanoate and (3R)-3-(t-butyldimethylsilyloxy)-6-dimethoxyphosphinyl-5-oxo-hexanoate. These intermediates are prepared by a novel intermediate i.e. chiral base salt of hydroxy protected diethyl glutarate.

US 2005/0070605 A1 discloses the enantioselective opening of 3-hydroxy protected glutaric anhydride by phenylethylamine to form an amide bond, and further conversion to obtain the HMG-CoA reductase inhibitor.

The compound 3(R)-3(tert-butyldimethylsilyloxy)-5-oxo-6-triphenyl-phosphoranylidene hexanoate can be prepared from the pentanoic acid derivatives of the following Formula-II.

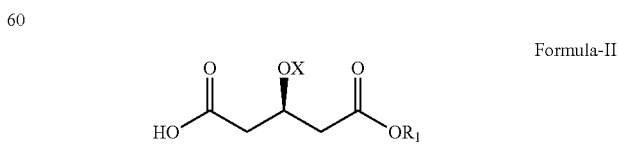

Formula-II wherein X is hydrogen or hydroxy protecting group and $R_1$ is carboxyl protecting group.

In prior art compound of Formula-II is prepared by the resolution of the racemate or asymmetric synthesis. These routes have disadvantages in the industrial scale preparation. The present invention provides an industrially scalable process for the pentanoic acid derivatives of Formula-II and further conversion to HMG-CoA reductase inhibitors.

OBJECT AND SUMMARY OF THE INVENTION

The principle object of the present invention is to provide novel process for the preparation of pentanoic acid derivatives of Formula-II and further conversion into HMG-CoA reductase inhibitors.

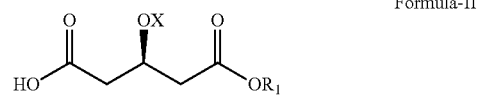

Formula-II wherein X is hydrogen or hydroxy protecting group and $R_1$ is carboxyl protecting group.

One aspect of the present invention provides, process for the preparation of compound of Formula-II comprising the steps of:
a) enzymatic enantioselective amidation of compound of Formula-III in presence of suitable enzyme to get amide compound of Formula-IV

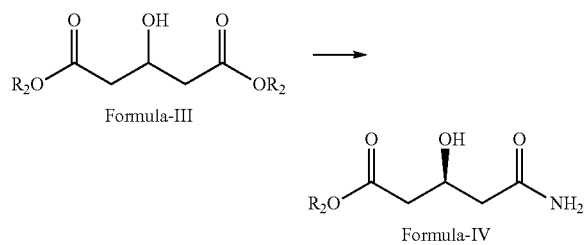

wherein $R_2$ is $C_1$-$C_5$ alkyl or aryl or arylalkyl group;
b) transesterification of compound of Formula-IV into compound of Formula-V

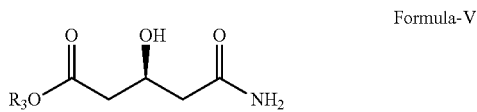

Formula-V wherein $R_3$ is $C_1$-$C_5$ alkyl or aryl or arylalkyl group with proviso that $R_3$ is different than the $R_2$ of Formula-IV;
c) protecting the hydroxy group with suitable hydroxy protecting group to get compound of Formula-VI

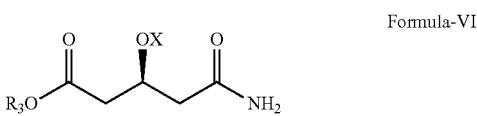

Formula-VI wherein X is suitable protecting group;
d) converting the compound of Formula-VI into compound of Formula-VII; and

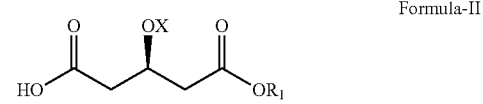

Formula-VII e) converting compound of Formula-VII into compound of Formula-II.

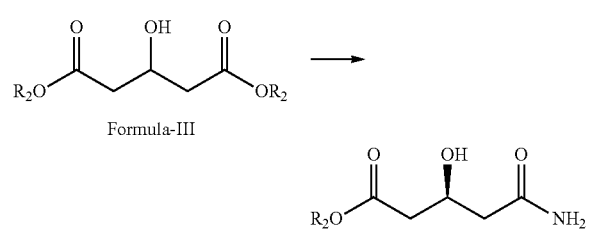

Formula-II wherein $R_1$ is carboxyl protecting group and X is defined above.

DETAILED DESCRIPTION OF THE INVENTION

The present invention relates to novel process for the preparation of pentanoic acid derivatives of compound of Formula-II, used as intermediates of HMG-CoA reductase inhibitors and further conversion to HMG-CoA reductase inhibitors.

The compound of Formula-II is used in the preparation of heptenoate side chain intermediates of HMG-CoA reductase inhibitors.

One aspect of the present invention provides process for the preparation of compound of Formula-II comprising the steps of:
a) enzymatic enantioselective amidation of compound of Formula-III in presence of suitable enzyme to get amide compound of Formula-IV

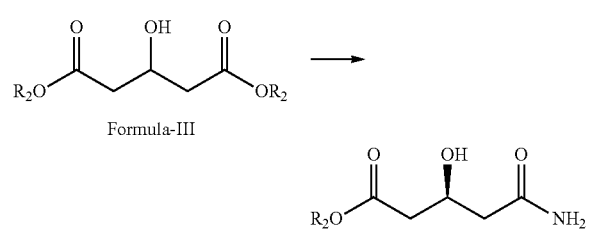

wherein $R_2$ is $C_1$-$C_5$ alkyl or aryl or arylalkyl group;
b) transesterification of compound of Formula-IV into compound of Formula-V

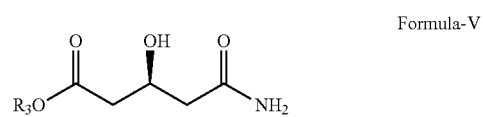

Formula-V wherein $R_3$ is $C_1$-$C_5$ alkyl or aryl or arylalkyl group with proviso that $R_3$ is different than $R_2$ of Formula-IV;
c) protecting the hydroxy group with suitable hydroxy protecting group to get compound of Formula-VI

Formula-VI wherein X is a suitable protecting group;
d) converting the compound of Formula-VI into compound of Formula-VII; and

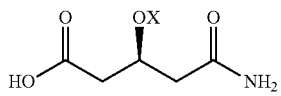

Formula-VII e) converting compound of Formula-WI into compound of Formula-II

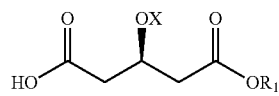

Formula-II wherein $R_1$ is carboxyl protecting group and X is defined above.

$R_1$ of the present invention is selected from carboxyl protecting group and X is hydroxy protecting group. Suitable protecting groups are available in the literature and well familiar to the person skilled in the art. Examples of suitable protecting groups can be found in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and or in Jochen Lehmann, "Chemie der Kohlenhydrate: Monosaccharide und Derivate", Georg Thieme Verlag, Stuttgart 1974. Preferable carboxyl protecting groups are $C_1$-$C_5$ alkyl, aryl, arylalkyl, more preferably $C_1$-$C_5$ alkyl.

Suitable hydroxy protecting groups are alkyl, aryl, arylalkyl, trialkylsilyl and diarylalkylslyl. Preferably trialkylsilyl or diarylalkylslyl. The protecting groups are trimethylsilyl, tert-butyldimethylsilyl, tert-butyldiphenylsilyl or diphenyl (tert-butyl)silyl group.

As per the present invention, in step-a, compound of formula III is selectively amidified by using enzyme. The enzyme used in this reaction is selected from hydrolytic enzymes, e.g. lipases, esterases, proteases. The preferred enzymes are microbial lipases that show amidation activity of esters with ammonia or amines in organic media. Exceptional performance is obtained by using lipases from the *Candida* genus, especially the *Candida antartica* lipase. The isoenzyme B is most preferred. To obtain acceptable activity for hydrolases in organic media, immobilization of the enzyme on a porous solid support is advantageous. The suitable enzyme used is an immobilized version of *Candida antartica* lipase B using anhydrous ammonia in an organic solvent. The organic solvent used in this step is an alcohol solvent or ethereal solvent. The alcohol solvent is selected from ethanol, methanol, isopropanol, tert-butanol or 2-methylbutan-2-ol (tert-Pentanol), 2-methyl-2-butanol, preferably tert-Pentanol. The ethereal solvent is selected from tetrahydrofuran, diethyl ether, methyl tert-butyl ether (MTBE), 2-methyltetrahydrofuran, cyclopentyl methyl ether, 1,4-dioxane, dimethoxyethane, diethyleneglycol diemthyl ether, preferably 1,4-dioxane. The obtained monoamide ester intermediate compound of Formula-IV is recrystallized to highly enantiomeric compound of Formula-IV.

The step-b of this invention involves transesterification of compound of Formula-IV. The transesterification of the compound of Formula-IV is carried out in presence of catalyst.

The suitable catalyst is selected from catalysts, which shows high transesterification activity under essentially neutral conditions, as the compounds of formula IV and formula V show limited optical stability under the usual strongly basic transesterification conditions. Catalysts that are active under essentially neutral conditions are dialkyltindialkoxide (e.g. dibutyltin dimethoxide) and tetraalkyl esters of titanium, e.g. tetramethyl orthotitanate, tetraethyl orthotitanate, tetrapropyl orthotitanate, tetraisopropyl orthotitanate, tetrabutyl orthotitanate and tetrabenzyl orthotitanate. Most preferred is the commercially available tetraisopropyl orthotitanate. In a special embodiment the tetraisopropyl orthotitanate can be first mixed with excess benzyl alcohol under vacuum to produce a solution of tetrabenzyl orthotitanate in benzyl alcohol. In this reaction very less amount of catalyst is used. The compound of Formula-IV is reacted with respective alcohol compound to yield required ester. In this reaction preferably araylalkyl ester, more preferably benzyl ester is prepared by reacting compound of Formula-IV with benzyl alcohol. The preferable catalyst used in this reaction is titanium catalyst and the titanium catalyst needs to be removed from the product. In most procedures this involves addition of some water to form insoluble hydrated $TiO_2$, but this generates a precipitate with unfavorable filtration properties. An alternative workup process has been developed, in which the reaction mixture is added to an aqueous solution of (DL/meso) tartaric acid: The tartaric acid forms a water soluble and stable titanium complex, while releasing the benzyl amidoester to the organic phase.

The step-c of this invention involves protection of the compound of Formula-V. The compound of Formula-V is protected by suitable protecting group such as alkyl, aryl, arylalkyl, trialkylsilyl and diarylalkylslyl in presence of base and organic solvent. The suitable protecting group used in this reaction is tert-Butyldimethylsilyl group. The base is selected from tertiary aliphatic amines or secondary aromatic or tertiary aromatic amines such as triethyl amine, diisopropylethylamine, N-methyl morpholine, pyridine, 4-dimethylaminopyridine, DBU, DBN, imidazole and N-methylimidazole, preferably imidazole. The organic solvent used in this reaction is a polar aprotic solvent, such as dichloromethane, chloroform, 1,2-dichloroethane, trifluoromethylbenzene, dimethylformamide, dimethylacetamide, N-methylpyrrolidone, dimethylsulfoxide, sulfolane, acetonitrile, benzonitrile, preferably dimethylformamide.

The step-d of this invention involves conversion of compound of Formula-VI to compound of Formula-WI. This conversion can be carried out by hydrolysis or catalytic hydrogenation of compound of Formula-VI. The catalytic hydrogenation of compound of Formula-VI is takes place in the presence of catalyst selected from transition metals that show hydrogenolysis of benzyl ester, preferably palladium on a solid support like Pd/C or Pd/Al$_2$O$_3$, preferably Pd catalyst in presence of hydrogen in an ester, alcohol, ether or aromatic solvents, preferably ester solvent. The preferable ester solvent is ethyl acetate.

The step-e of this invention involves the conversion of compound of Formula-VII into compound of Formula-II by the conversion of the amide to an ester. The reaction involves usage of dimethylformamide dimethylacetal under mild basic conditions. Under mild basic conditions this reagent converts the amide to a reactive acylformamidine, which then reacts with alcohols to form the corresponding ester, while it suppresses the esterification of the free carboxylic acid group. The base used in this reaction is selected from alkalimetal alkoxides like sodium methoxide or potassium methoxide, preferably sodium methoxide. The solvent used in this reaction is methanol.

Advantages of the Present Invention

The current reaction scheme avoids the use of chiral auxiliaries, cryogenic reaction conditions and yields an overall higher yield of desired optically pure monoester of formula II. The low amount of enzyme used in the first step can be recycled and reused many times, thus improving the production cost of the desired product. Many of the intermediates are crystalline solids that can be upgraded in chemical and optical purity by crystallization.

The compound of Formula-III is prepared by the prior art process as disclosed in Tetrahedron; 43(1); 45-58; 1987, Canadian journal of chemistry; 66(6); 1422-4; 1988 and Journal of the American chemical society; 68; 721; 1946.

The compound of Formula-II is further converted into HMG-CoA reductase inhibitors of Formula-I by the conventional methods as disclosed in U.S. RE 37,314, U.S. Pat. No. 5,260,440, WO 2003087112, US 2007037979 and CN 100506796.

For example the compound of Formula-II is further converted into Rosuvastatin calcium by the following procedure as depicted in the below scheme.

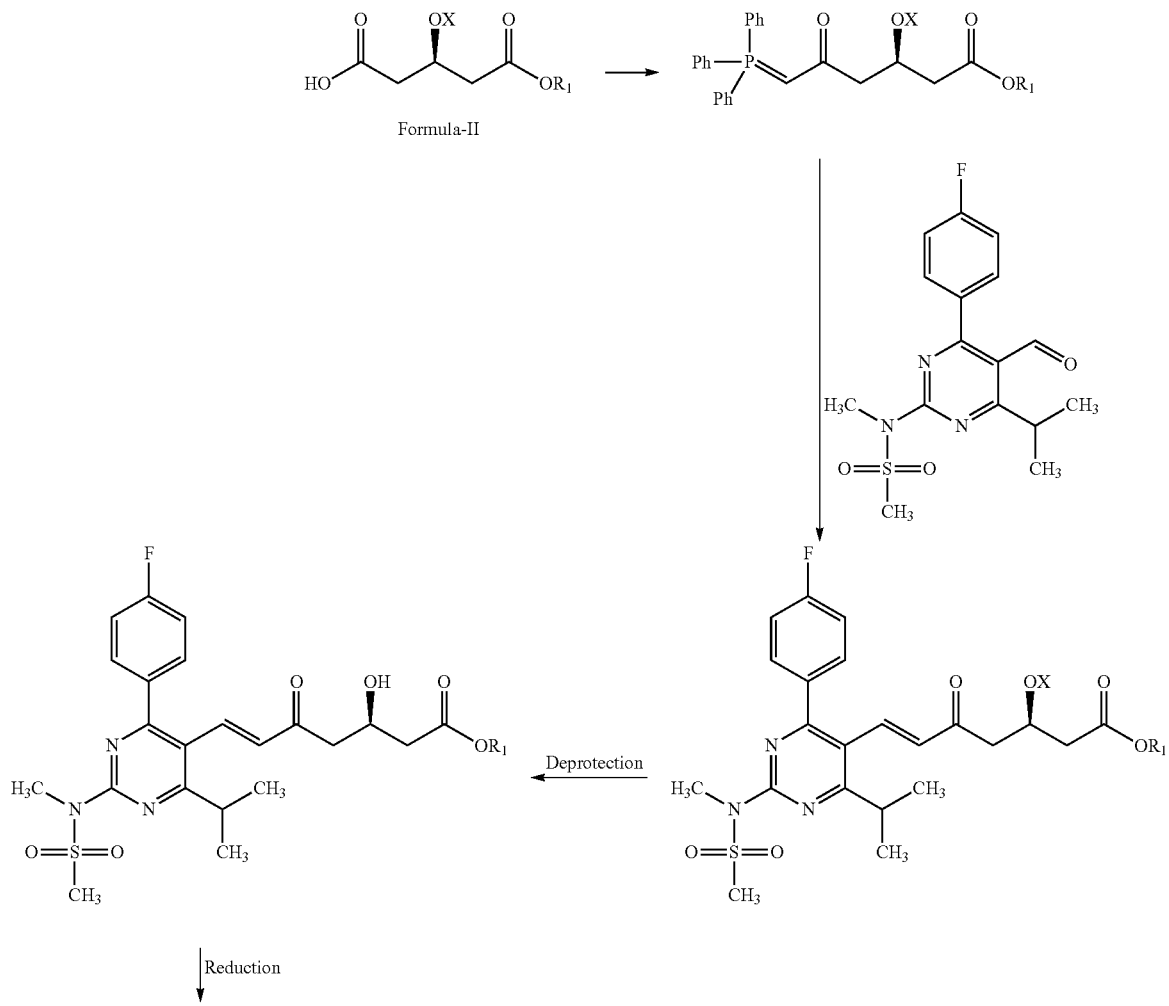

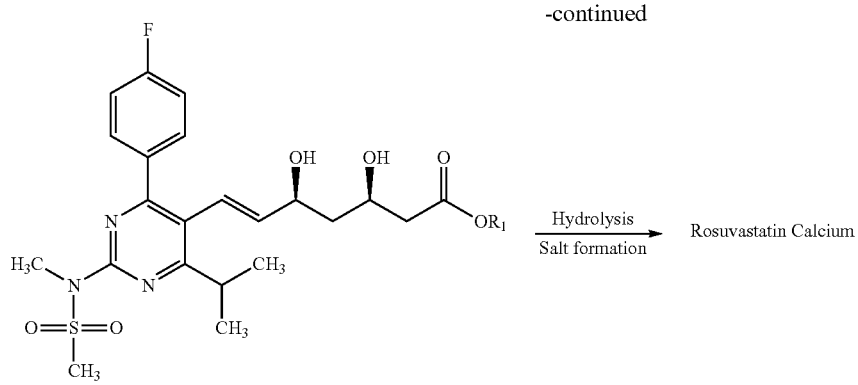
For example the compound of Formula-II is further converted into Pitavastatin calcium by the following procedure as depicted in the below scheme.
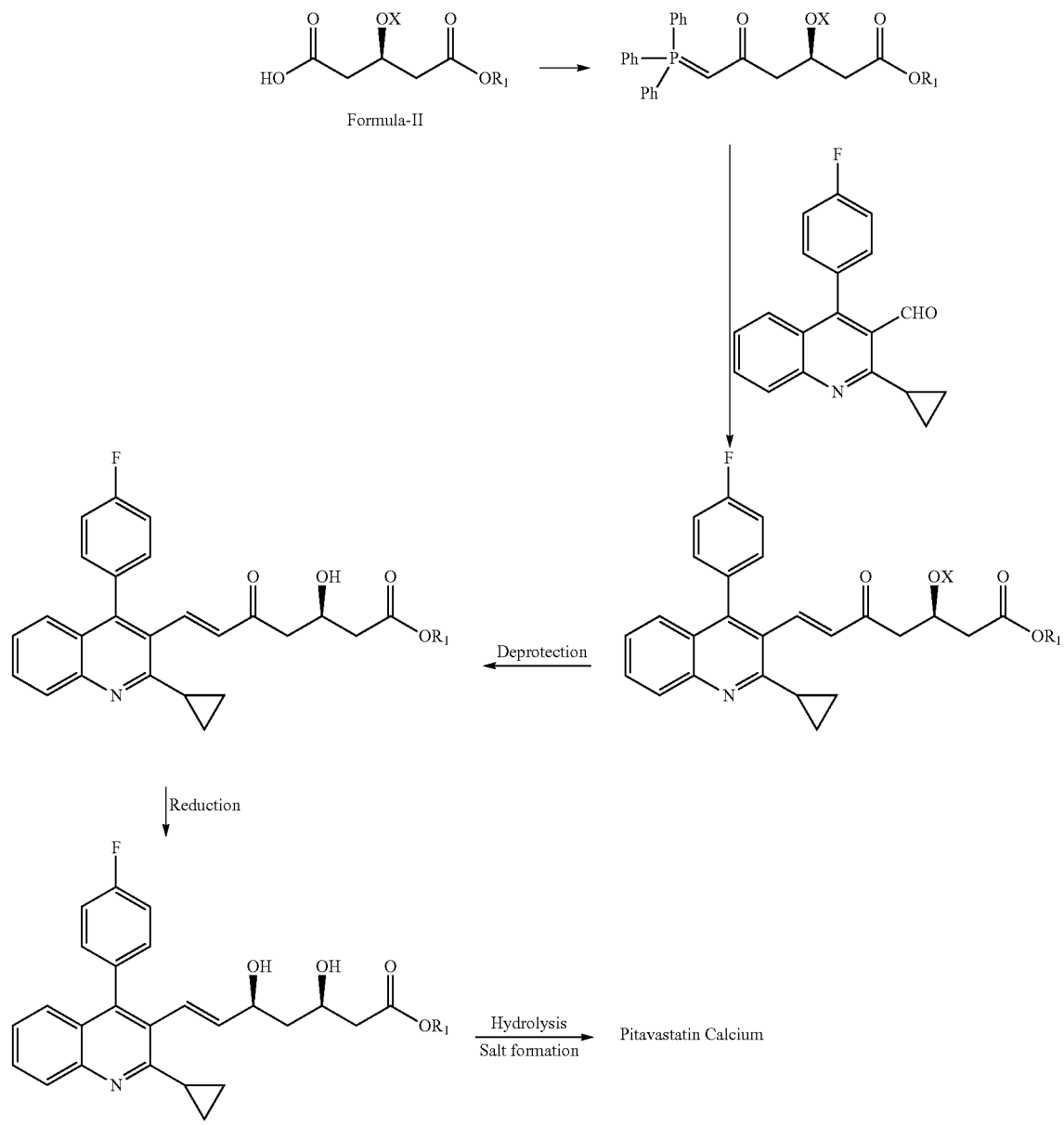

All patents, patent applications, and non-patent publications cited herein by reference should be considered in their entirety. The invention is illustrated with the following examples, which are provided by way of illustration only and should not be construed to limit the scope of the invention.

EXPERIMENTAL PROCEDURE

Example-1

Process for the Preparation of Compound of Formula-IV (where $R_2$=Me)

Tert-Pentanol (1.1 L) was saturated with gaseous ammonia until about 1 mol (17 g) has been evaporated from the ammonia cylinder. To this Compound of Formula-III ($R_2$=Me) (125 g; 0.71 mol) was added, followed by the addition of immobilized CAL-B (CAL-B-T1-350; 12.5 g). The reactor was closed and mechanically stirred at ambient temperature. After completion of the reaction enzyme was removed by filtration over a 100 µm sieve and washed with methanol. The filtrate evaporated under reduced pressure at a temperature below 50° C. to yield an oily residue. This residue was purified by crystallization from isopropyl acetate to yield (S)-Methyl 3-hydroxyglutaramate.

Example-2

Process for the Preparation of Compound of Formula-V (where $R_3$=Benzyl)

(S)-Methyl 3-hydroxyglutaramate obtained from example-1 (16.1 g; 0.1 mol) was mixed with benzyl alcohol (25 g). The mixture was heated under vacuum (<15 mbar) at 55° C. to remove traces of moisture. Neat tetraisopropyl orthotitanate (3 ml; 10 mol %) was added and the mixture heated under full vacuum for 3 h at 55-57° C. The mixture was cooled and diluted with 1 volume of Tetrahydrofuran. The organic mixture was slowly added in 10 m to a vigorously stirred mixture of aqueous tartaric acid (1 M, 100 ml) and ethyl acetate. The organic phase was removed and the aqueous phase extracted with ethyl acetate. The combined organic extracts were washed with dilute sodium bicarbonate solution. The organic phase was evaporated under reduced pressure and MTBE was added and the mixture cooled with stirring. The obtained thick suspension was filtered and washed with cold MTBE and pentane to yield (S)-Benzyl 3-hydroxyglutaramate.

Example-3

Process for the Preparation of Compound of Formula-VI (where $R_3$=Benzyl and X=Tert-butyldimethylsilyl)

A mixture of (S)-Benzyl 3-hydroxyglutaramate (66 g; 0.28 mol; 97% e.e.) and imidazole (23 g; 0.34 mol; 1.2 eq.) was mixed with dimethylformamide (70 ml). To this mixture a solution of tert-Butyldimethylsilyl chloride (45 g; 0.3 mol) in dimethylformamide (150 ml) was added under cooling (+5° C.). The mixture was warmed to 25° C. and stirred for 1 hour. The mixture was quenched with water. The mixture was diluted further with water and extracted with isopropylacetate. The organic extract was washed with water and diluted with sodium bicarbonate and brine. After evaporation (S)-Benzyl 3-[tert-butyldimethylsilyloxy]glutaramate as an oil was obtained.

Example-4

Process for the Preparation of Compound of Formula-VII (where X=Tert-butyldimethylsilyl)

(S)-Benzyl 3-[tert-butyldimethylsilyloxy]glutaramate from example-3 (48.5 g) was dissolved in ethyl acetate (350 ml) and placed in a 500 ml glass pressure reactor with magnetic stirring. Palladium on charcoal catalyst (5%, 0.48 g) was added to this and the mixture was hydrogenated under 2.7 atmosphere of hydrogen for 4 hours. The pressure was released and the mixture was filtered. The catalyst was washed with 25 ml ethyl acetate and kept for reuse. The filtrate was mixed with water. The pH of the mixture was adjusted to 8.5 using 2.5 M aqueous ammonia under stirring. The aqueous phase was extracted once with MTBE. The clear aqueous phase was cooled to +5° C. and slowly acidified to pH 4.4 using conc HCl. A thick precipitate was formed at pH 4.8-5. The mixture was filtered and the solid was washed once with water and dried under reduced pressure to yield (S)-3-[tert-butyldimethylsilyloxy]glutaric acid monoamide.

Example-5

Process for the Preparation of Compound of Formula-II (where X=Tert-butyldimethylsilyl and R1=Me)

(S)-3-[tert-Butyldimethylsilyloxy]glutaric acid monoamide (4.6 g) was dissolved under argon atmosphere in anhydrous methanol (30 ml). The pH of the reaction mixture was adjusted to 11.4 by the addition of sodium methoxide solution (3.6 ml 30%). The solution was mixed under argon with 5.0 g of dimethylformamide dimethylacetal (42 mmol). The mixture was stirred under inert atmosphere for 20 h at 30° C. The obtained mixture was slowly added to a stirred mixture of dichloromethane and dilutes phosphoric acid. The organic phase was washed with water and evaporated to give (R)-Methyl 3-[tert-butyldimethylsilyloxy]glutarate.

Example-6

Process for the Preparation of (S)-methyl-3-hydroxyglutaramate

Tert-pentanol (800 ml) was saturated with ammonia gas to about 1.0-1.5 mole. To this dimethyl-3-hydroxy glutarate (100 g) was added followed by the addition of 3 g immobilized CAL-B(CAL B-T1-AMD2). The flask was closed and stirred at 20-25° C. After completion of reaction enzyme was removed by filtration and washed the enzyme with tert-pentanol (100 ml). The filtrate was evaporated under reduced pressure at a temperature below 50° C. to yield a residue. This residue was purified by crystallization from tert-pentanol/tert-butyl methyl ether mixture to give (S)-methyl-3-hydroxyglutaramate.

Example-7

Process for the Preparation of (S)-Benzyl-3-hydroxyglutaramate

Mixture of Benzyl alcohol (131.0 g), (S)-methyl-3-hydroxyglutaramate (100 g) and Tetraisopropyl orthotitanate (17.5 g) are mixed in a flask. The mixture was stirred under vacuum at 50-60° C. for about 5 hrs. The reaction mixture was cooled and diluted with isopropyl acetate (500 ml). The reaction mixture was added to a stirred solution of Tartaric acid (37 g in 370 ml DM water) and 500 ml isopropyl acetate mixture. The reaction mixture was stirred and pH was adjusted to 7.0-8.0 by Aq ammonia solution. Layers were separated. The organic phase was removed and the aqueous phase was extracted with isopropyl acetate. Combined organic layer was washed with Aq ammonia and tartaric acid solution followed by brine wash. The organic phase was dried over anhydrous sodium sulphate and evaporated under reduced pressure to yield oil. To this oil tert-butyl methyl ether (800 ml) was added, stirred, cooled, filtered and dried to give (S)-Benzyl-3-hydroxyglutaramate.

Example-8

Process for the Preparation of (S)-Benzyl-3-hydroxyglutaramate

Mixture of Benzyl alcohol (131.0 g), (S)-methyl-3-hydroxyglutaramate (100 g) and Tetraisopropyl orthotitanate (17.5 g) are mixed in a flask. The mixture was stirred under vacuum at 50-60° C. for about 5 hrs. The reaction mixture was cooled and diluted with dichloromethane (500 ml). The reaction mixture was added to a stirred solution of Tartaric acid (37 g in 370 ml DM water) and 500 ml dichloromethane mixture. The reaction mixture was stirred and pH was adjusted to 7.0-8.0 by Aq ammonia solution. Layers were separated. The organic phase was removed and the aqueous phase was extracted with dichloromethane. Combined organic layer was washed with Aq ammonia and tartaric acid solution followed by brine wash. The organic phase was dried over anhydrous sodium sulphate and evaporated under reduced pressure to yield oil. To this oil tert-butyl methyl ether (800 ml) was added, stirred, cooled, filtered and dried to give (S)-Benzyl-3-hydroxyglutaramate.

Example-9

Process for the Preparation of (S)-benzyl-3-(tert-butyl dimethylsilyloxy)glutaramate (S)-Benzyl-3-hydroxyglutaramate (100 g) was dissolved in dimethyl formamide. To this Imidazole (35 g) was added and the solution was cooled to 5° C. To this a solution of tert-butyldimethylsilylchloride (68.5 g) dissolved in dimethyl formamide (250 ml) was added under cooling. The mixture was warmed to 20-25° C. and stirred. The reaction mixture was cooled and quenched with water. To the reaction mixture ethyl acetate and water was added and stirred. The layers were separated and the organic phase was washed thrice with water. The organic phase was evaporated under reduced pressure to yield (S)-benzyl-3-(tert-butyl dimethylsilyloxy)glutaramate as oil.

Example-10

Process for the Preparation of (S)-3-(tert-butyl dimethylsilyloxy)glutaric acid monoamide (S)-Benzyl-3-(tert-butyl dimethylsilyloxy)glutaramate (100 g) was dissolved in ethyl acetate and placed in pressure flask. To this Palladium on charcoal (5%, 1 g) was added and stirred under hydrogen atmosphere (~2.8 Kg). Palladium was removed by filtration. The filtrate was mixed with water and adjusted pH to ~9.0 by using Aq ammonia solution. The reaction mass was stirred and layers were separated. The aqueous phase was washed with dichloromethane and dichloromethane was added to aqueous phase. The reaction mass was cooled to 5° C. and pH was adjusted to 4.0 with Aq phosphoric acid. The reaction mass was stirred and layers were separated. The organic phase was washed with water and dried over sodium sulphate. The organic layer was evaporated under vacuum to yield residue. Residue was dissolved in dichloromethane and to this solution heptane was added, stirred, filtered and dried to yield (S)-3-(tert-butyl dimethylsilyloxy)glutaric acid monoamide.

Example-11

Process for the Preparation of (S)-3-(tert-butyl dimethylsilyloxy)glutaric acid monoamide (S)-Benzyl-3-(tert-butyl dimethylsilyloxy)glutaramate (100 g) was dissolved in ethyl acetate and placed in pressure flask. To this Palladium on charcoal (5%, 1 g) was added and stirred under hydrogen atmosphere (~2.8 Kg). Palladium was removed by filtration. The filtrate was mixed with water and adjusted pH to ~9.0 by using Aq ammonia solution. The reaction mass was stirred and layers were separated. The aqueous phase was washed with dichloromethane and dichloromethane was added to aqueous phase. The reaction mass was cooled to 5° C. and pH was adjusted to 4.0 with Aq phosphoric acid. The reaction mass was stirred and layers were separated. The organic phase was washed with water and dried over sodium sulphate. The organic layer was evaporated under vacuum to yield residue. Residue was dissolved in dichloromethane and to this solution pentane was added, stirred, filtered and dried to yield (S)-3-(tert-butyl dimethylsilyloxy)glutaric acid monoamide.

Example-12

Process for the Preparation of (S)-3-(tert-butyl dimethylsilyloxy)glutaric acid monoamide (S)-Benzyl-3-(tert-butyl dimethylsilyloxy)glutaramate (100 g) was dissolved in ethyl acetate and placed in pressure flask. To this Palladium on charcoal (5%, 1 g) was added and stirred under hydrogen atmosphere (~2.8 Kg). Palladium was removed by filtration. The filtrate was mixed with water and adjusted pH to ~9.0 by using Aq ammonia solution. The reaction mass was stirred and layers were separated. The aqueous phase was washed with dichloromethane and dichloromethane was added to aqueous phase. The reaction mass was cooled to 5° C. and pH was adjusted to 4.0 with Aq phosphoric acid. The reaction mass was stirred and layers were separated. The organic phase was washed with water and dried over sodium sulphate. The organic layer was evaporated under vacuum to yield residue. Residue was dissolved in dichloromethane and to this solution hexane was added, stirred, filtered and dried to yield (S)-3-(tert-butyl dimethylsilyloxy)glutaric acid monoamide.

Example-13

Process for the Preparation of (R)-Methyl-3-(tert-butyldimethylsilyloxy)glutarate (S)-3-(tert-butyl dimethylsilyloxy)glutaric acid monoamide (100 g) was dissolved in methanol (650 ml) under nitrogen atmosphere. The reaction mass was ~25% Sodium methoxide solution (82.9 g) was added under cooling. Then reaction mass was heated to ~25° C. and to this dimethyl formamide dimethylacetal (100 g) was slowly added. The mixture was stirred for ~20 hrs at 25° C. The reaction mass was slowly added to a stirred mixture of dichloromethane and diluted phosphoric acid solution. Layers were separated. The organic phase was washed thrice with water, dried over sodium sulphate and evaporated under reduced pressure to yield (R)-Methyl-3-(tert-butyldimethylsilyloxy)glutarate.

Example-14

Process for the Preparation of (S)-Benzyl-3-hydroxyglutaramate

Tert-pentanol (800 ml) was saturated with ammonia gas to about 1.0-1.5 mole. To this dimethyl-3-hydroxy glutarate (100 g) was added followed by the addition of 3 g immobilized CAL-B (CAL B-T1-AMD2). The flask was closed and stirred at 20-25° C. After completion of reaction enzyme was removed by filtration and washed the enzyme with tert-pentanol (100 ml). The filtrate was evaporated under reduced pressure at a temperature below 50° C. to yield a residue. To this residue mixture of Benzyl alcohol (131.0 g), (S)-methyl-3-hydroxyglutaramate (100 g) and Tetraisopropyl orthotitanate (17.5 g) are mixed in a flask. The mixture was stirred under vacuum at 50-60° C. for about 5 hrs. The reaction mixture was cooled and diluted with isopropyl acetate (500 ml). The reaction mixture was added to a stirred solution of Tartaric acid (37 g in 370 ml DM water) and 500 ml isopropyl acetate mixture. The reaction mixture was stirred and pH was adjusted to 7.0-8.0 by Aq ammonia solution. Layers were separated. The organic phase was removed and the aqueous phase was extracted with isopropyl acetate. Combined organic layer was washed with Aq ammonia and tartaric acid solution followed by brine wash. The organic phase was dried over anhydrous sodium sulphate and evaporated under reduced pressure to yield oil. To this oil tert-butyl methyl ether (800 ml) was added, stirred, cooled, filtered and dried to give (S)-Benzyl-3-hydroxyglutaramate.

Example-15

Process for the Preparation of (S)-3-(tert-butyl dimethylsilyloxy)glutaric acid monoamide (S)-Benzyl-3-hydroxyglutaramate (100 g) was dissolved in dimethyl formamide. To this Imidazole (35 g) was added and the solution was cooled to 5° C. To this a solution of tert-butyldimethylsilylchloride (68.5 g) dissolved in dimethyl formamide (250 ml) was added under cooling. The mixture was warmed to 20-25° C. and stirred. The reaction mixture was cooled and quenched with water. To the reaction mixture ethyl acetate and water was added and stirred. The layers were separated and the organic phase was washed thrice with water. To the organic phase Palladium on charcoal (5%, 1 g) was added and stirred under hydrogen atmosphere (~2.8 Kg). Palladium was removed by filtration. The filtrate was mixed with water and adjusted pH to ~9.0 by using Aq ammonia solution. The reaction mass was stirred and layers were separated. The aqueous phase was washed with dichloromethane and dichloromethane was added to aqueous phase. The reaction mass was cooled to 5° C. and pH was adjusted to 4.0 with Aq phosphoric acid. The reaction mass was stirred and layers were separated. The organic phase was washed with water and dried over sodium sulphate. The organic layer was evaporated under vacuum to yield residue. Residue was dissolved in dichloromethane and to this solution heptane was added, stirred, filtered and dried to yield (S)-3-(tert-butyl dimethylsilyloxy)glutaric acid monoamide.

Example-16

Process for the Preparation of (S)-methyl-3-hydroxyglutaramate

Tert-pentanol (200 ml) was saturated with anhydrous ammonia at ambient pressure. This was cooled to ambient temperature and to this CaLB-T1-AMD enzyme (1.25 g) and dimethyl 3-hydroxyglutarate (25.3 g) were added. The resulting mixture was gently stirred with a magnetic stirrer at ambient temperature (20-21° C.) for 18 h. The enzyme was removed by filtration and washed with tert-pentanol (25 ml). The clear filtrate (200 g) was concentrated under reduced pressure at a maximum temperature of +50° C. to light brown oil. The oil was again dissolved in tert-pentanol (90 ml) and placed in a mechanically stirred 500 ml vessel. To this MTBE (Methyl tert-butyl ether) was slowly added under seeding with methyl (S)-3-hydroxyglutaramate (10 mg). The crystal suspension was cooled in an ice-bath to +5° C. The reaction mass was filtered, washed with MTBE and dried to yield (S)-methyl-3-hydroxyglutaramate.

Example-17

Process for the Preparation of (S)-Benzyl-3-hydroxyglutaramate (S)-Methyl-3-hydroxyglutaramate (41.2 g) and benzyl alcohol (54 g) were placed in a 250 ml flask. This mixture was heated under vacuum to 55° C. to get clear solution. To this neat tetraisopropyl orthotitanate (7.5 ml) was added. The mixture was rotated at 55-58° C. under vacuum. The reaction mixture was diluted with isopropyl acetate and added to a solution of tartaric acid (7.5 g in 50 ml water) and isopropyl acetate (200 ml). The organic phase was removed and washed with water, NaHCO$_3$-solution and brine. The organic phase was dried over sodium sulfate and evaporated to blue oil. The aqueous phases were additionally extracted with ethyl acetate to yield colorless oil. The combined oily material was mechanically stirred with MTBE and seeded with (S)-Benzyl-3-hydroxyglutaramate. The thick suspension was cooled in an ice-bath to 5° C. and aged for 15 m, followed by filtration. The solid was washed with MTBE and pentane (50 ml). The resulting was dried to yield (S)-Benzyl-3-hydroxyglutaramate.

Example-18

Process for the Preparation of (S)-benzyl-3-(tert-butyl dimethylsilyloxy)glutaramate (S)-Benzyl-3-hydroxyglutaramate (49.5 g) was dissolved in anhydrous dimethylformamide (50 ml) and added to a 500 ml flask containing solid imidazole (17.1 g). To this a solution of tert-butyldimethylsilyl chloride (34 g) in dimethylformamide (120 ml) was added and reaction flask was cooled in an ice-bath. The reaction was quenched by addition of water-saturated ethyl acetate. The mixture was stirred at ambient temperature. To this water was added and the biphasic mixture was stirred for 1 hour. The mixture was then washed with water. The organic phases were mixed and washed with water to remove traces of dimethylformamide. The organic phase was evaporated under reduced pressure to yield (S)-benzyl-3-(tert-butyl dimethylsilyloxy)glutaramate.

Example-19

Process for the Preparation of (S)-3-(tert-butyl dimethylsilyloxy)glutaric acid monoamide (S)-benzyl-3-(tert-butyl dimethylsilyloxy)glutaramate (70 g) was dissolved in ethyl acetate (350 ml) and placed in a 500 ml glass pressure vessel. To this dry 5% Pd/C (1.4 g) was added under vacuum and pressurized with hydrogen gas at 2.7 bar overpressure. The mixture was stirred magnetically while remaining connected to the hydrogen source. The catalyst was removed by filtration and washed with a small volume of ethyl acetate (25 ml). The clear filtrate was mixed with water and dilute ammonia. The aqueous phase was isolated and the organic phase extracted with water. The combined aqueous phase was washed with MTBE and degassed under vacuum to remove traces of organic solvent. The mixture was placed in an ice-bath. The cooled aqueous solution was acidified using dilute phosphoric acid to obtain thick suspension. This was filtered, washed with cold water and dried to yield (S)-3-(tert-butyl dimethylsilyloxy)glutaric acid monoamide.

Example-20

Process for the Preparation of (R)-Methyl-3-(tert-butyldimethylsilyloxy)glutarate (S)-3-(tert-butyl dimethylsilyloxy)glutaric acid monoamide (10 g) was dissolved in anhydrous methanol (90 ml) and placed under Argon. To this mixture sodium methoxide solution (8.6 g) was added. To this neat dimethylformamide dimethyl acetal (10 g) was added and the resulting mixture stirred under Argon at 30° C. for 16 hours. The mixture was cooled and added to a pre cooled mixture of ethyl acetate (150 ml) and aqueous citric acid (19 g in 100 ml water). To the resulting homogeneous mixture MTBE and brine was added. The organic phase was washed twice with water and dried using a brine wash and sodium sulfate. The dried solution was carefully evaporated to yield (R)-Methyl-3-(tert-butyldimethylsilyloxy)glutarate.

We claim:
1. A process for the preparation of compound of Formula-II comprising the steps of:
a) enzymatic enantioselective amidation of compound of Formula-III in presence of suitable enzyme to get amide compound of Formula-IV

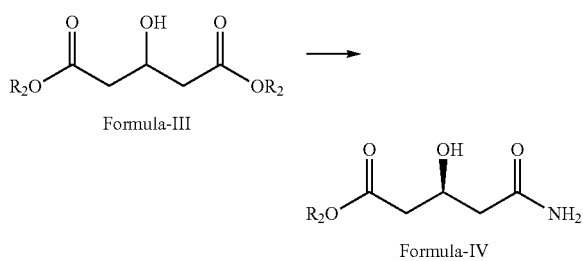

wherein $R_2$ is $C_1$-$C_5$ alkyl or aryl or arylalkyl group and wherein said suitable enzyme is *Candida Antartica* lipase;

b) transesterification of compound of Formula-IV into compound of Formula-V

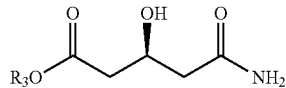

Formula-V wherein $R_3$ is $C_1$-$C_5$ alkyl or aryl or arylalkyl group with proviso that $R_3$ is different than $R_2$ of Formula-IV;
c) protecting the hydroxy group with suitable hydroxy protecting group to get compound of Formula-VI

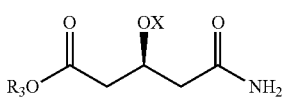

Formula-VI wherein X is a suitable protecting group;
d) converting the compound of Formula-VI into compound of Formula-VII; and

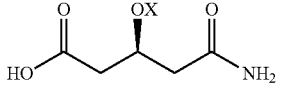

Formula-VII e) converting compound of Formula-VII into compound of Formula-II

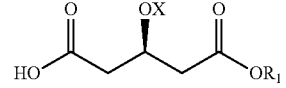

Formula-II wherein $R_1$ is carboxyl protecting group and X is defined above.

2. The process according to claim 1, wherein lipase is *Candida Antartica* lipase B.

3. The process according to claim 1, wherein $R_3$ is arylalkyl group in compound of Formula-V.

4. The process according to claim 1, wherein transesterification of the compound of Formula-IV is carried out in presence of catalyst.

5. The process according to claim 4, wherein catalyst is selected from tetramethyl orthotitanate, tetraethyl orthotitanate, tetrapropyl orthotitanate, tetraisopropyl orthotitanate, tetrabutyl orthotitanate or tetrabenzyl orthotitanate.

6. The process according to claim 1, wherein compound of Formula-VI is converted into compound of Formula-VII by catalytic hydrogenation.

7. The process according to claim 1, wherein $R_1$ is $C_1$-$C_5$ alkyl group in compound of Formula-II.

8. The process according to claim 1, wherein compound of Formula-II is further converted into HMG-CoA reductase inhibitors.

9. The process according to claim 8, wherein the HMG-CoA reductase inhibitor is Rosuvastatin or Pitavastatin.

* * * * *